United States Patent [19]
Bauman

[11] Patent Number: 5,695,049
[45] Date of Patent: Dec. 9, 1997

[54] CONTACT LENS PACKAGE WITH INSERTION FEATURE

[75] Inventor: Robert C. Bauman, Litchfield, Conn.

[73] Assignee: Johnson & Johnson Vision Products, Inc., Jacksonville, Fla.

[21] Appl. No.: 727,994

[22] Filed: Oct. 10, 1996

[51] Int. Cl.$^6$ .................. A61F 9/00; B65D 85/38
[52] U.S. Cl. .................. 206/5.1; 206/804; 294/1.2; 606/107
[58] Field of Search .............. 206/5.1, 210, 804; 128/898, 899; 294/1.2; 606/107; 623/4

[56] References Cited

U.S. PATENT DOCUMENTS

| | | |
|---|---|---|
| 3,424,486 | 1/1969 | Corley. |
| 3,791,689 | 2/1974 | Boone et al.. |
| 4,026,591 | 5/1977 | Cleaveland. |
| 4,326,742 | 4/1982 | Ingram ............ 294/1.2 |
| 5,114,686 | 5/1992 | Gillespie ............ 206/5.1 |
| 5,348,358 | 9/1994 | Selick ............ 294/1.2 |
| 5,407,062 | 4/1995 | Shannon et al.. |
| 5,467,868 | 11/1995 | Abrams et al.. |
| 5,474,169 | 12/1995 | Bauman. |
| 5,515,964 | 5/1996 | Bauman. |
| 5,609,246 | 3/1997 | Borghorst et al. ............ 206/5.1 |

FOREIGN PATENT DOCUMENTS 3822654  1/1990  Germany.

Primary Examiner—Jimmy G. Foster
Attorney, Agent, or Firm—Pepe & Hazard

[57] ABSTRACT

A contact lens container comprising an integrally molded one-piece synthetic resin receptacle providing a well having a peripheral wall with a bottom portion, and a flange extending about the periphery of the upper end of well. The bottom portion has a generally concave inner surface for seating a contact lens thereon and is being relatively rigid. The peripheral wall of the well has an annular, resiliently deflectable inversion portion above the bottom portion, and it is invertible to position the bottom portion of the well above the plane of the flange. Pressing upwardly against the bottom portion of the well inverts the inversion portion of the well and dispose the bottom portion with the lens thereon above the plane of the flange. The receptacle is moved against the eye of the user to place the lens against the cornea and thereby cause the lens to seat thereon.

23 Claims, 5 Drawing Sheets

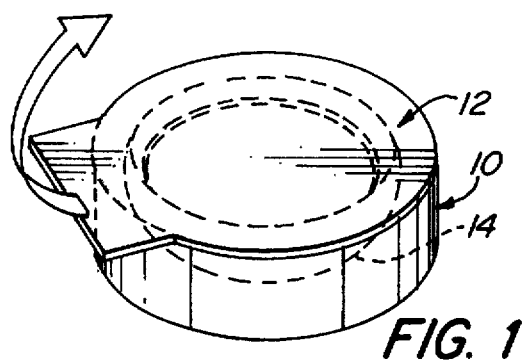
FIG. 1
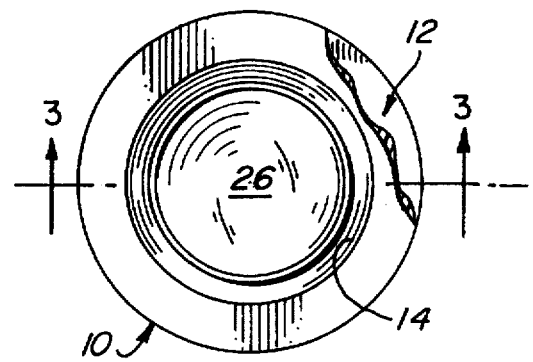
FIG. 2
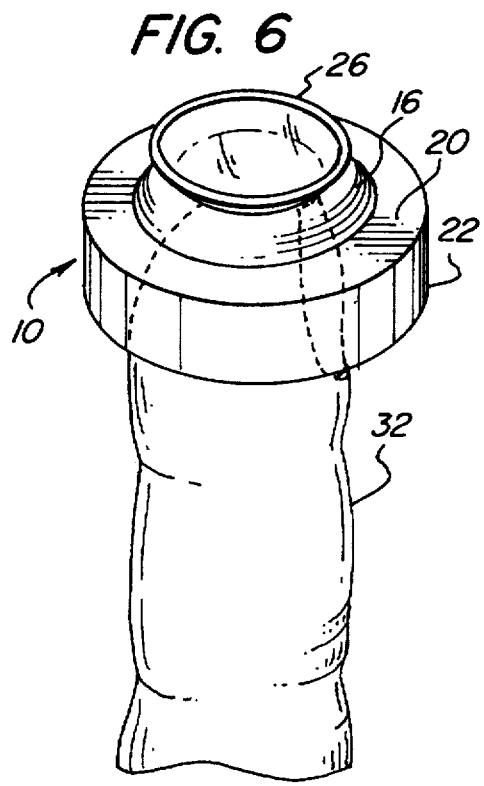
FIG. 6
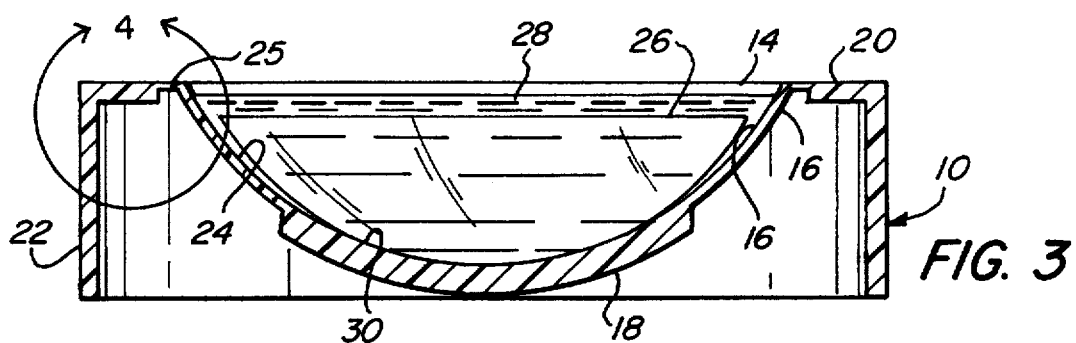
FIG. 3
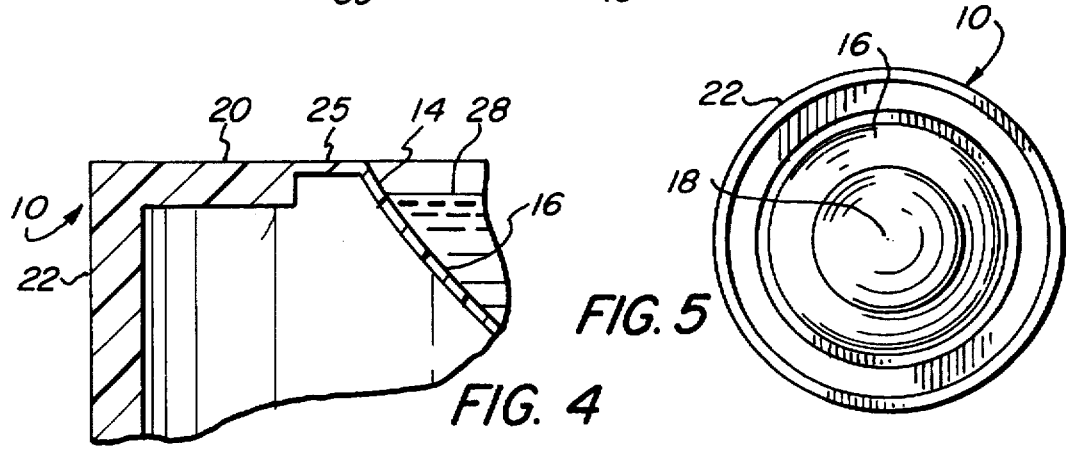
FIG. 4
FIG. 5

CONTACT LENS PACKAGE WITH INSERTION FEATURE

BACKGROUND OF THE INVENTION

The present invention relates to contact lens storage containers and, more particularly, to a storage container for contact lenses which will also provide a means for insertion of the lens into the eye.

Many different types of containers have been used for storage of contact lenses including durable molded structures with replaceable covers intended for repeated use. Other containers are relatively low cost disposable structures which store the lens only prior to opening and are thereafter discarded.

In addition, a number of devices have been developed to facilitate the placement of a contact lens on the cornea of the eye rather than transfer the lens to a finger to do so. This is particularly true when hygienic conditions are desired. Such devices require an additional item to be carried with the user, cleanliness for the applicator, and transfer of the lens from the container to the applicator.

In my earlier U.S. Pat. Nos. 5,474,169 and 5,515,964, I have disclosed a number of different types of disposable lens storage containers which, although providing low cost and easily utilized containers which are capable of maintaining the lens in a specific orientation, do not enable use of the container to place the lens in the eye.

It is an object of the present invention to provide a novel contact lens storage container which may be utilized to facilitate placement of the lens into the eye without contact with the user's finger.

It is also an object to provide such a contact lens storage container which may be fabricated relatively economically and easily.

Still another object is to provide such a contact lens container which may be utilized repeatedly through employment of a replaceable closure.

A further object is to provide such a contact lens container which maintains the lens in the desired orientation for placement in the eye.

Yet another object is to provide a novel method for storage of a contact lens in a container during shipment and handling and for utilization of the container as a means for sterile placement of the lens onto the cornea of the eye.

SUMMARY OF THE INVENTION

It has now been found that the foregoing and related objects may be readily attained in a contact lens container comprising an integrally molded one-piece synthetic resin receptacle providing a well having a peripheral wall terminating in a bottom portion. A flange extends about the periphery of the upper end of the peripheral wall, and the bottom portion has a generally concave inner surface for seating a contact lens thereon and is relatively rigid. The peripheral wall of the well has an annular, resiliently deflectable inversion portion above the bottom portion which is invertible to position the bottom portion of the well above the plane of the flange.

The well is of a generally circular cross section which generally decreases in diameter towards the bottom portion. Desirably, the peripheral wall of the well has at least one retention element on its inner periphery above the bottom portion to retain a contact lens on the seating surface. A multiplicity of peripherally spaced ribs are preferably provided on the inner periphery of the peripheral wall and extend inwardly of the well to provide the retention elements.

In the usual embodiments, the peripheral wall of the well has a reduced thickness to provide the deflectable inversion portion. However, the deflectable inversion portion of the peripheral wall may differ in composition from the remainder of the well.

Generally, the deflectable inversion portion extends to the upper end of the peripheral wall and into the flange, and the well is inverted about the flange. In some embodiments, the deflectable inversion portion includes at least one annular step adjacent the upper end thereof, and some may include a series of annular steps.

Desirably, the receptacle includes a peripheral skirt depending from the outer end of the flange and the skirt extends below the well to provide a stable support for seating the receptacle on a support surface. The skirt may have inwardly extending projections defining a passage in which a user's finger may be snugly seated, and the projections are preferably resiliently deflectable.

The container includes a closure releasably engaged with the receptacle and sealing the well, and it may be planar and is adhered to the flange. Alternatively, the receptacle may include a peripheral skirt depending from outer end of the flange, and the closure has a depending peripheral portion threadably engaged with the skirt.

In use of the receptacle to insert a contact lens into the eye, providing a contact lens receptacle comprising an integrally molded one-piece synthetic resin receptacle providing a well having a peripheral wall terminating in a bottom portion, and a flange extending about the periphery of the upper end of the peripheral wall, the bottom portion having a generally concave inner surface for seating a contact lens thereon and being relatively rigid, the closure is removed and the user presses upwardly against the bottom portion of the well to invert the inversion portion of the well and dispose the bottom portion with the lens thereon above the plane of the flange. The user then moves the receptacle against the eye of the user to place the lens against the cornea and thereby cause the lens to seat thereon.

BRIEF DESCRIPTION OF THE DRAWINGS

FIG. 1 is a perspective view of a lens storage container embodying the present invention with an arrow indicating the direction in which the closure is removed;

FIG. 2 is a top plan view of the lens storage container of FIG. 1 with the closure broken away;

FIG. 3 is a sectional view thereof along line 3—3 of FIG. 2 with the closure removed and drawn to an enlarged scale;

FIG. 4 is an enlarged portion of FIG. 3;

FIG. 5 is a bottom view of the receptacle of FIG. 3;

FIG. 6 is a perspective view of the receptacle of FIG. 1 showing an index finger pushing upwardly to invert a section of the receptacle well thereby enabling it to be used as an insertion device for placing the lens on the cornea;

DETAILED DESCRIPTION OF THE PREFERRED EMBODIMENTS

Figure 7:
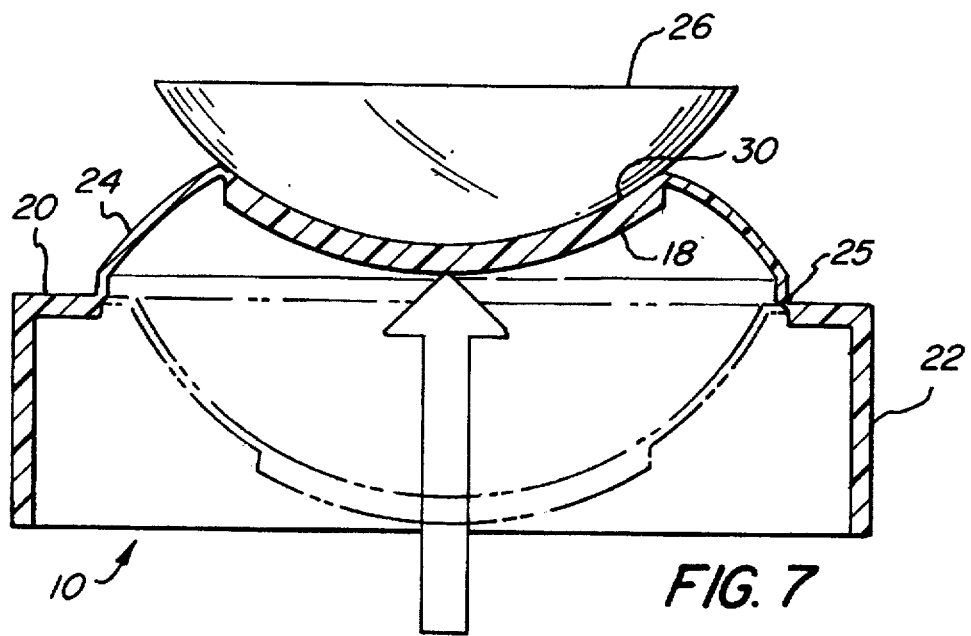
FIG. 7 is a sectional view similar to FIG. 3 showing the well inverted with an arrow showing the force being applied to the bottom portion of the well, and the lens seating portion being elevated thereby.

Turning first to FIGS. 1-3, therein illustrated is a contact lens container for storing and inserting a contact lens into the eye. It is generally comprised of a receptacle generally designated by the numeral 10 and a closure generally designated by the numeral 12 which may be removed therefrom.

As seen best in FIG. 3, the receptacle 10 comprises a well 14 provided by a peripheral wall 16 and a bottom portion 18, and a flange 20 extends outwardly therefrom about the entire periphery of the well 14. At the outer edge of the flange 20 is a peripheral skirt 22 which depends therefrom to a point just below the bottom surface of the bottom portion 18 of the well 14 as best illustrated in FIG. 3.

As illustrated in FIGS. 4 and 5, the peripheral wall 16 of the well 14 has a reduced wall thickness indicated by the area 24 and a flange 20 has a contiguous reduced wall thickness indicated by the numeral 25.

Seated on the concave inner surface 3 of the bottom portion 18 is a contact lens designated by the numeral 26 surrounded by a saline solution indicated by the numeral 28.

As seen in FIGS. 6 and 7, the finger 32 of the user may be pushed upwardly, of the outer surface of the bottom portion 18 to push it upwardly thus causing the reduced wall portions 24 and 25 to invert the upper portion of the peripheral wall 16 to provide a pedestal extending above the plane of the flange 20 and exposing the outer peripheral portion of the contact lens 26. Obviously, in the process of doing so, saline solution about the contact lens will also be expelled, although some saline solution may be retained within the contact lens itself.

Figure 8:
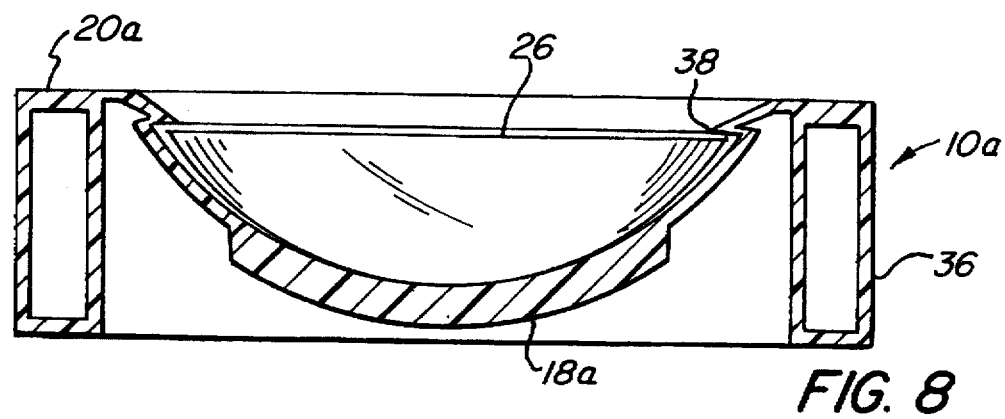
FIG. 8 is a sectional view similar to FIG. 3 of another embodiment of the contact lens storage receptacle embodying the present invention.

Although the skirt 22 illustrated in the embodiment of FIGS. 1-7 will provide stable seating for the receptacle on a contact surface such as a table, desk, sink or the like, in some instances it may be desirable to provide even more stability or durability in the event of a reusable container. In this instance, the embodiment of FIGS. 8 and 9 utilizes a box-like skirt 36 providing an enhanced area for stable seating of the receptacle on a support surface.

Figure 9:
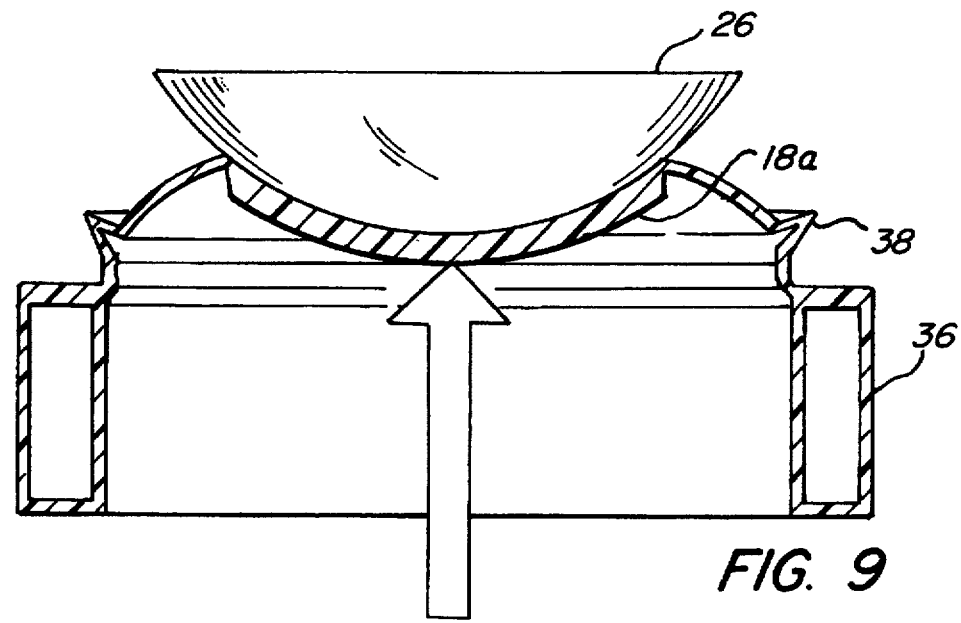
FIG. 9 is a sectional view of the receptacle of FIG. 8 with an arrow showing the force applied to the bottom of the well to effect inversion.

In this embodiment, the peripheral wall 16a of the well 14a also has an inwardly extending step or lip 38 on the inner surface thereof adjacent its upper end. The lip serves to retain the contact lens 26 in the position in which it is placed upon the bottom portion 18 and also to provide a formation which facilitates inversion of the well 14 as seen in FIG. 9.

Figure 10:
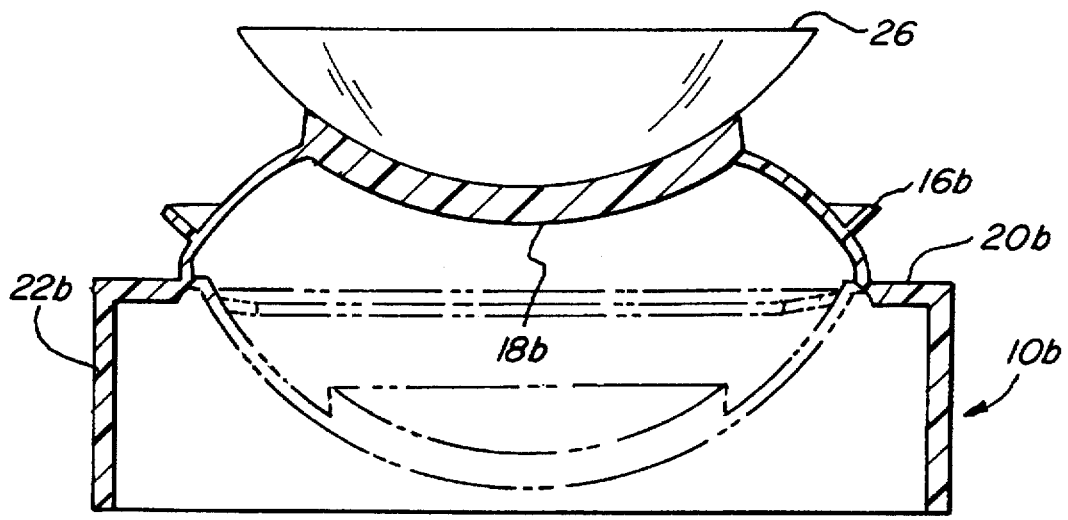
FIG. 10 is a view similar to FIG. 7 of another embodiment of a lens storage container embodying the present invention in the inverted position.

Turning next to FIG. 10, therein illustrated is still another embodiment in which the peripheral wall 16b has a rib-like projections 38b thereon for retaining the contact lens 26 seated on the concave seating surface provided by the bottom portion 18b.

Figure 11:
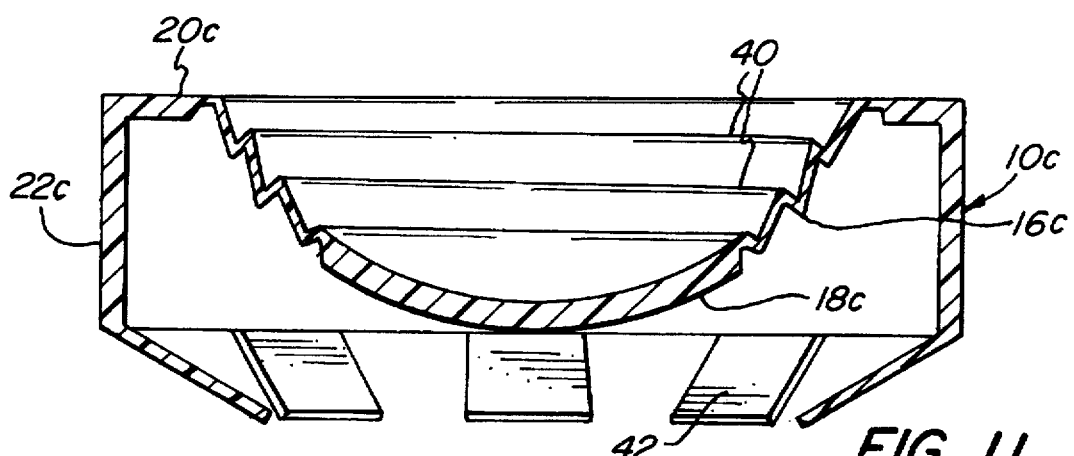
FIG. 11 is a view similar to FIG. 3 of another embodiment of a lens storage receptacle embodying the present invention.
Figure 12:
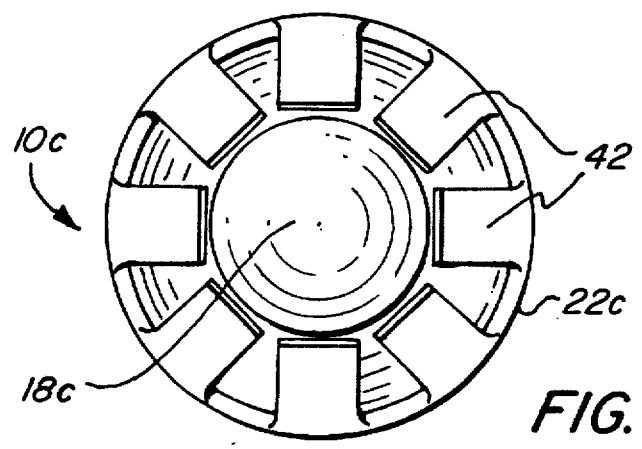
FIG. 12 is a bottom view of the lens storage receptacle of FIG. 11 drawn to a reduced scale.

Turning next to FIGS. 11 and 12, the embodiment therein has a peripheral wall 16c provided by a series of steps 40 providing the equivalent of a flexible bellows in the reduced wall thickness providing the invertible wall portion. In addition, the skirt 22c has a series of inwardly extending resiliently deflectable fingers 42 which may be deflected upon insertion of the user's finger thereinto and which will grip tightly about the user's finger to facilitate manipulation of the receptacle 10c during the insertion of the lens into the eye.

Figure 13:
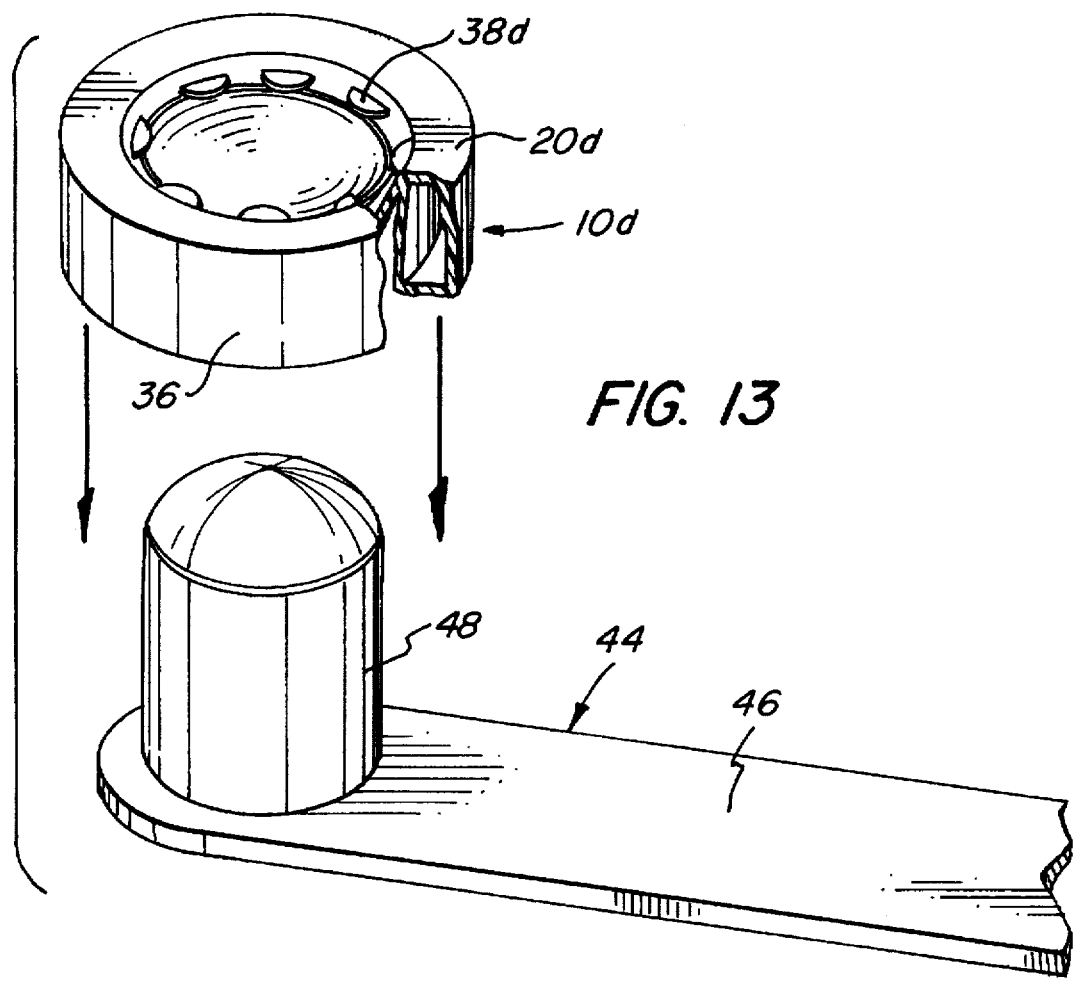
FIG. 13 is a perspective view of still another embodiment of a lens storage receptacle embodying the present invention and a manipulator fragmentarily illustrated with arrows showing the container being placed upon its pedestal.
Figure 14:
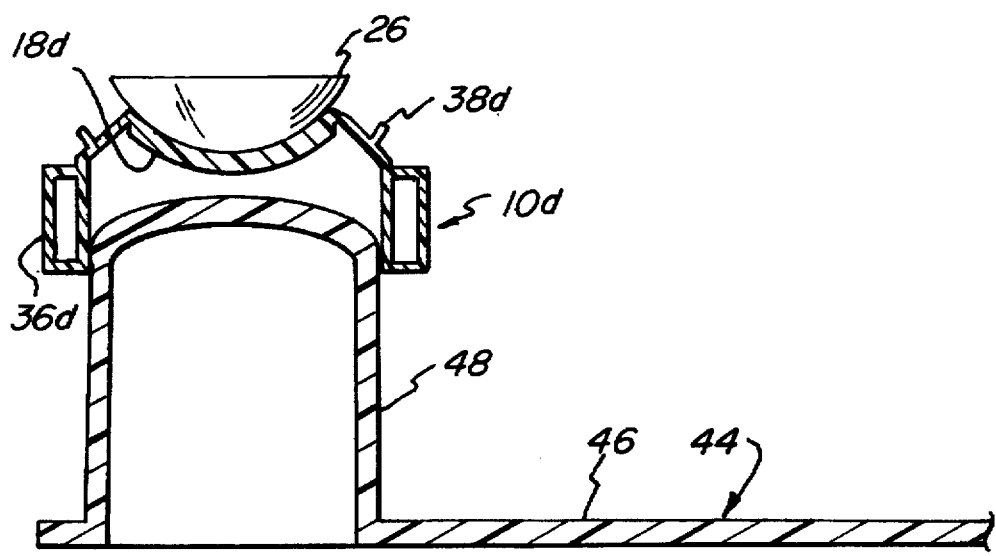
FIG. 14 is a sectional view of the receptacle of FIG. 13 showing the container placed upon the manipulator and the well inverted.

In the embodiments of FIGS. 13 and 14, the receptacle 10b has a series of ribs 38c spaced about its inner periphery and a box-like skirt 36c. In this instance, an insertion device generally designated by the numeral 44 has an elongated arm portion 46 and a cylindrical pedestal 48 at one end thereof which can be inserted snugly into the space within the skirt 36d to both push upwardly upon the bottom portion 18d to effect the inversion of the wall 16d and to also provide the means for engagement of the insertion device 44 therewith. Thus, the arm 46 may be used for manipulation of the receptacle 10 with the lens 26 seated therein rather than requiring the user's finger or fingers to effect the manipulation of the receptacle 10b.

Figure 15:
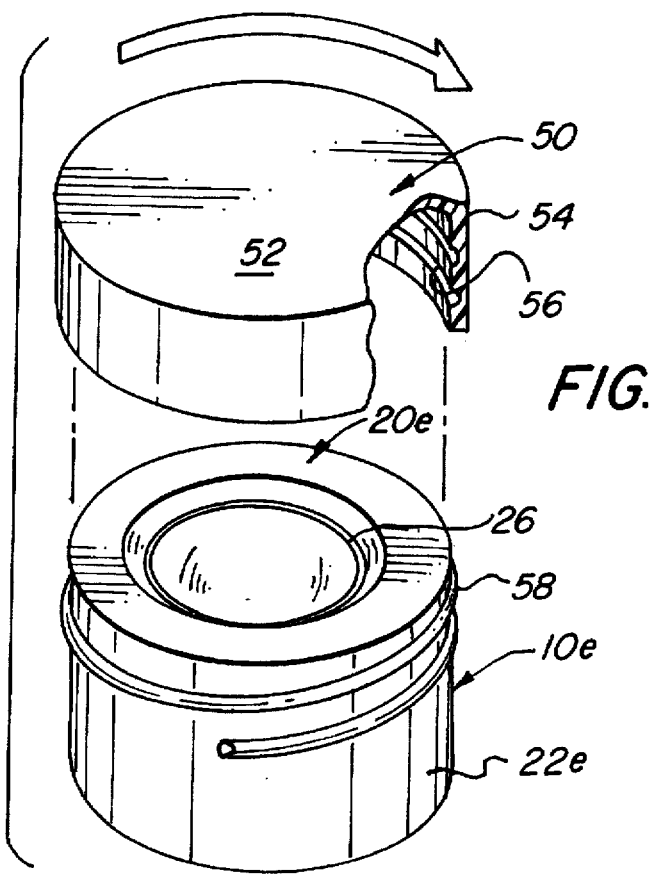
FIG. 15 is a fragmentary perspective view of another embodiment of a lens storage container embodying the present invention with a threaded cap.

In the embodiment of FIG. 15, this employs a flanged closure generally designated by the numeral 50 with a top wall 52 and a side wall 54 provided with internal threads 56. The skirt 22e of this embodiment is provided with external threads 58 to provide for threaded coupling of the closure 50 and receptacle 10e.

Figure 16:
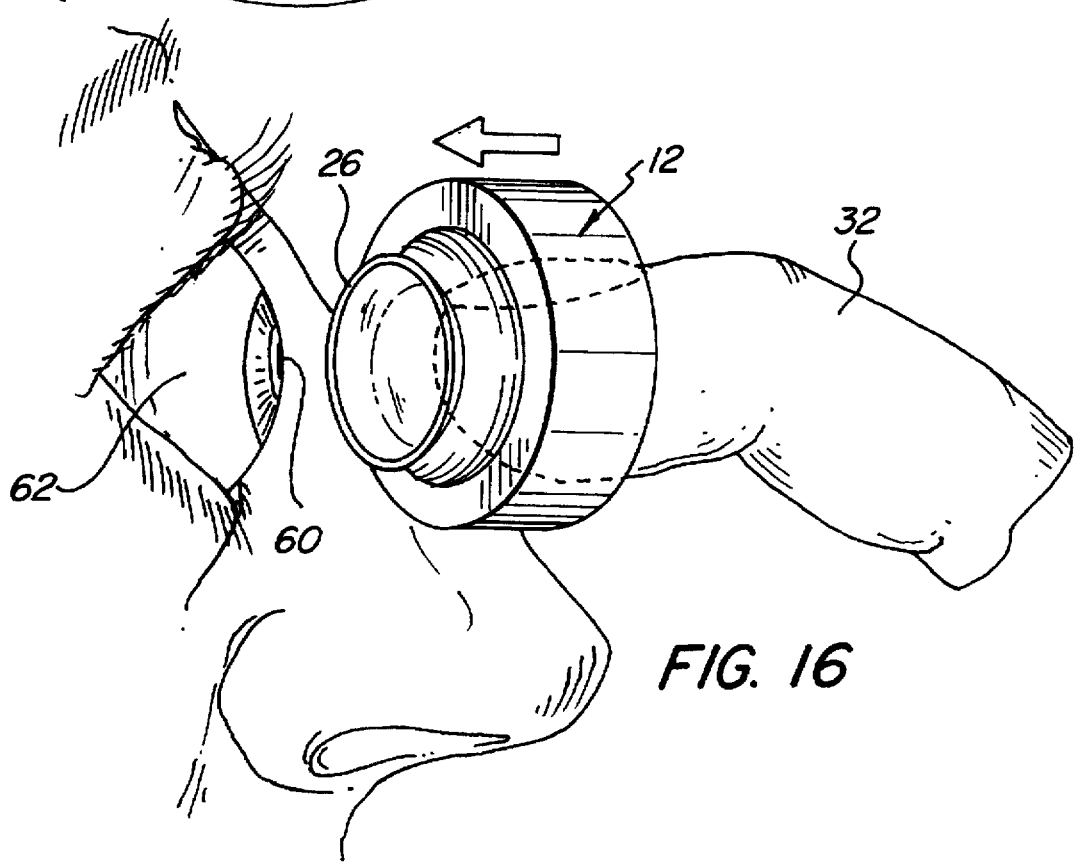
FIG. 16 is a view showing the inverted receptacle being moved against the cornea to place the lens thereon.

Lastly, there is illustrated in FIG. 16 the manner in which the pedestal provided by the inverted well 14 may be used to place the lens 26 against the corner 60 so that it will transfer from the concave surface 36 to the surface of the cornea 60. The radius of curvature of the inner surface of the bottom portion 18 of the well should approximate the radius of curvature of the human cornea, or be about 5.7 to 11.7 millimeters and preferably about 8.7 millimeters. In this manner, the lens will tend to be retained in position on the concave surface by reason of surface attraction.

In using the storage container of the present invention, the manufacturer of the contact lens places the lens in the well in the desired orientation, i.e., with the outer surface of the lens seated against the concave surface of the well. As a result, because of the similarity of curvature, the lens will be maintained in position on the concave surface of the well. The embodiments which employ a lip or ribs spaced about the periphery of the inside surface of the well, the lip or ribs will keep the lens in position despite sudden movements or impacts which would tend to displace the lens from the surface of the well.

The receptacle of the lens storage container in the several embodiments is readily formed from synthetic resin by injection molding although thermoforming and compression molding may also be employed. The dimensions of the lip or ribs can be very small since they need only resist movement of the lens outwardly along the surface; as little as 0.005 inch of an inward projection will be sufficient. By proper selection of the resins and the configuration of the mold, the projections can be formed in one step without the requirements for special plugs.

Various resins may be employed to form the receptacle including polyethylene, polypropylene and ethylene vinyl acetate which are relatively economical. The resins employed may be modified in composition in the inversion area to provide the invertability or the wall thickness may be reduced as illustrated in the indicated embodiments. When a planar closure is employed, this is conveniently a metallic foil or foil/resin laminate using adhesive or a foil with a layer of a thermoplastic resin which will enable heat sealing to provide a suitable bond to the flange.

Thus, it can be seen from the foregoing detailed description and attached drawings that the lens storage container of the present invention not only provides convenient storage of the lens but also maintains it in a predetermined orientation and enables the receptacle to be employed as the means for placement of the lens onto the cornea so as to minimize contact with the hand and maintain a highly hygienically condition. Moreover, the receptacle and the closure may be readily fabricated from economical materials to provide a relatively low cost container which can be disposable or reusable.

Having thus described the invention, what is claimed is:

1. A contact lens container comprising an integrally molded one-piece synthetic resin receptacle providing a well having a peripheral wall terminating in a bottom portion, and a flange extending about the periphery of the upper end of said peripheral wall, said bottom portion having a generally concave inner surface for seating a contact lens thereon and being relatively rigid, said peripheral wall of said well having an annular resiliently deflectable inversion portion above said bottom portion, said inversion portion being invertible to position said bottom portion of said well above the plane of said flange.

2. The contact lens container according to claim 1 wherein said well is of generally circular cross section.

3. The contact lens container according to claim 2 wherein said cross section of said well generally decreases in diameter towards said bottom portion.

4. The contact lens container according to claim 1 wherein said peripheral wall of said well has at least one retention element on its inner periphery above said bottom portion to retain a contact lens on said seating surface.

5. The contact lens container according to claim 4 wherein a multiplicity of peripherally spaced ribs on said inner periphery of said peripheral wall extend inwardly of said well to provide retention elements.

6. The contact lens container according to claim 1 wherein said peripheral wall of said well has a reduced thickness to provide said deflectable inversion portion.

7. The contact lens container according to claim 1 wherein said deflectable inversion portion of said peripheral wall differs in composition from the remainder of said well.

8. The contact lens container according to claim 1 wherein said deflectable inversion portion extends to the upper end of said peripheral wall and into said flange.

9. The contact lens container according to claim 8 wherein said well is inverted about said flange.

10. The contact lens container according to claim 1 wherein said deflectable inversion portion includes at least one annular step adjacent the upper end thereof.

11. The contact lens container according to claim 1 wherein said deflectable inversion portion includes a series of annular steps.

12. The contact lens container according to claim 1 wherein said receptacle includes a peripheral skirt depending from the outer end of said flange.

13. The contact lens container according to claim 12 wherein said skirt extends below said well to provide a stable support for seating said receptacle on a support surface.

14. The contact lens container according to claim 12 wherein said skirt has inwardly extending projections defining a passage in which a user's finger may be snugly seated.

15. The contact lens container according to claim 14 wherein said projections are resiliently deflectable.

16. The contact lens container according to claim 1 wherein said container includes a closure releasably engaged with said receptacle and sealing said well.

17. The contact lens container according to claim 16 wherein said closure is planar and is adhered to said flange.

18. The contact lens container according to claim 16 wherein said receptacle includes a peripheral skirt depending from outer end of said flange and said closure has a depending peripheral portion threadably engaged with said skirt.

19. A method for storing and inserting a contact lens into the eye comprising:

(a) providing a contact lens receptacle comprising an integrally molded one-piece synthetic resin receptacle providing a well having a peripheral wall terminating in a bottom portion, and a flange extending about the periphery of the upper end of said peripheral wall, said bottom portion having a generally concave inner surface for seating a contact lens thereon and being relatively rigid, said peripheral wall of said well having an annular resiliently deflectable annular inversion portion above said bottom portion, said inversion portion being invertible to position said bottom portion of said well above the plane of said flange;

(b) placing a contact lens on said seating surface of said well and a saline solution in said well;

(c) placing a closure on said receptacle to seal said well and retain said contact lens and saline solution therein;

(d) removing said closure;

(e) pressing upwardly against said bottom portion of said well to invert said inversion portion of said well and dispose said bottom portion with said lens thereon above the plane of said flange; and (f) moving said receptacle against the eye of the user to place said lens against the cornea and thereby cause said lens to seat thereon.

20. The contact lens sorting and inserting method in accordance with claim 19 wherein said providing step includes forming said receptacle with a depending skirt extending about the outer end of said flange.

21. The contact lens sorting and inserting method in accordance with claim 20 wherein the user inserts a finger to seat in said skirt.

22. The contact lens sorting and inserting method according to claim 21 wherein said step of forming includes providing inwardly extending deflectable projections on said skirt and said finger resiliently deflects said projections and is engaged therewith.

23. The contact lens sorting and inserting method according to claim 20 wherein a manipulator is inserted into and engaged with said skirt.

* * * * *